(12) United States Patent
Gomperz et al.

(10) Patent No.: US 6,763,270 B1
(45) Date of Patent: Jul. 13, 2004

(54) LEAD EXTRACTION MECHANISM FOR ACTIVE FIXATION LEADS

(75) Inventors: Benedict L. Gomperz, North Hollywood, CA (US); Russell Klehn, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 357 days.

(21) Appl. No.: 09/925,066

(22) Filed: Aug. 7, 2001

(51) Int. Cl.$^7$ .................................................. A61N 1/05
(52) U.S. Cl. ........................ 607/126; 607/122; 607/127; 606/108
(58) Field of Search .......................... 607/116, 119, 607/122, 126, 127; 606/108, 1; 600/585

(56) References Cited

U.S. PATENT DOCUMENTS

| | | | |
|---|---|---|---|
| 4,574,800 A | * 3/1986 | Peers-Trevarton | 606/1 |
| 4,790,825 A | 12/1988 | Bernstein et al. | 604/170 |
| 4,791,939 A | 12/1988 | Maillard | 128/786 |
| 4,924,881 A | 5/1990 | Brewer | 128/785 |
| 4,943,289 A | 7/1990 | Goode et al. | 606/1 |
| 4,957,118 A | 9/1990 | Erlebacher | 128/785 |
| 4,972,848 A | 11/1990 | Di Domenico et al. | 128/785 |
| 4,988,347 A | 1/1991 | Goode et al. | 606/1 |
| 5,011,482 A | 4/1991 | Goode et al. | 606/1 |
| 5,013,310 A | 5/1991 | Goode et al. | 606/1 |
| 5,020,545 A | 6/1991 | Soukup | 128/785 |
| 5,056,516 A | 10/1991 | Spehr | 128/419 P |
| 5,129,404 A | 7/1992 | Spehr et al. | 128/785 |
| 5,207,683 A | 5/1993 | Goode et al. | 606/108 |
| 5,231,996 A | 8/1993 | Bardy et al. | 128/785 |
| 5,234,002 A | 8/1993 | Chan | 128/772 |
| 5,259,395 A | 11/1993 | Li | 607/131 |
| 5,421,348 A | 6/1995 | Larnard | 128/772 |
| 5,447,534 A | 9/1995 | Jammet | 607/127 |
| 5,593,433 A | 1/1997 | Spehr et al. | 607/128 |
| 5,609,623 A | 3/1997 | Lindegren | 607/128 |
| 5,662,698 A | 9/1997 | Altman et al. | 607/123 |
| 5,769,858 A | 6/1998 | Pearson et al. | 606/108 |
| 5,800,497 A | 9/1998 | Bakels et al. | 607/122 |
| 5,807,399 A | 9/1998 | Laske et al. | 607/126 |
| 6,132,390 A | 10/2000 | Cookston et al. | 600/585 |
| 6,611,710 B2 | * 8/2003 | Gomperz et al. | 607/7 |

* cited by examiner

Primary Examiner—Kennedy Schaetzle

(57) ABSTRACT

A technique for removing from a body an implanted lead including an active fixation electrode includes the operation of releasably attaching an elongated stylet to the distal end of the implanted lead, specifically, to the electrode at the distal end of the lead. This results in a reasonably unified stylet and implanted lead structure whereby withdrawal of the stylet and of the implanted lead as a unit facilitates the complete removal of the implanted lead from the body. A threaded tip end of the stylet is used for threaded engagement with a tapped bore in the electrode. The threaded tip end of the stylet becomes locked to the electrode by rotating in one direction the threaded portion into the threaded bore and the stylet is removable by counter-rotating the threaded tip end of the stylet relative to the electrode.

8 Claims, 3 Drawing Sheets

LEAD EXTRACTION MECHANISM FOR ACTIVE FIXATION LEADS

FIELD OF THE INVENTION

The present invention relates to removal of an implanted lead extending between distal and proximal ends from a body and, more particularly, to a technique which facilitates the complete removal of the lead from the body.

BACKGROUND OF THE INVENTION

Lead extraction is required when an infection occurs and at times when products are upgraded or replaced. Current lead extraction techniques cut the connector from the lead, then mechanically lock into the lead conductor coil near the lead distal electrode. During lead extraction the distal end of the coil is deformed and the lead is no longer functional. There is a potential for lead fracture, resulting in incomplete extraction, and possibly requiring additional surgery to complete the procedure.

Typical of the known prior art are U.S. Pat. Nos. 5,013,310 and 5,011,482, both to Goode et al. which utilize a stylet wire which is inserted into the longitudinal passageway of an implanted lead, then secured at its distal end to the distal end of the implanted lead. Thereafter, the stylet wire is withdrawn and takes with it the implanted lead. U.S. Pat. No. 4,957,118 represents another example of the prior art in which an electrode lead is provided with a tine assembly having tines on an electrode tip which can be moved back and forth between a retracted position and an extended position. A threaded rod is rotatably mounted within the elongated body of the lead for moving the conductive electrode tip relative to the non-conductive tubular body. In a number of instances, as in U.S. Pat. No. 4,924,881 to Brewer, an implantable endocardial lead includes a retractable fixation device such as a sharpened helix. A threaded stylet passes through a lumen from a proximal end to a distal end of the lead where the stylet is screwed into a piston supporting the helix. When the helix is in an exposed position, torque can be transmitted by the stylet from the proximal end of the lead through the distal end to the piston and thence to the helix to screw the helix into the endocardial tissue. Similar constructions are disclosed in U.S. Pat. Nos. 5,129,404 and 5,593,433 to Spehr et al. and in U.S. Pat. No. 5,259,395 to Li.

U.S. Pat. No. 5,662,698 to Altman et al. discloses an implantable lead system that uses a locking stylet to adjust the insulation around the lead during implantation.

U.S. Pat. No. 5,769,858 to Pearson et al. discloses an implantable lead system that includes a locking stylet for extracting the lead wherein the locking lead interacts with a kinked distal tip to lock into the distal tip.

U.S. Pat. No. 5,800,497 to Bakels et al. discloses an implantable lead system that uses a magnetically interactive material that hardens in the presence of a magnetic field to lock a stylet into the lead during explant.

U.S. Pat. No. 5,807,399 to Laske et al. discloses a lead removal system that includes pulling the electrode within the lead and then collapsing the lead to remove it from the body.

It was in light of the foregoing that the present invention was conceived and has now been reduced to practice.

SUMMARY OF THE INVENTION

The present invention discloses a technique for removing an implanted lead from a body. This technique includes the operation of releasably attaching an elongated stylet to the distal end of the implanted lead, specifically, the electrode at the distal end of the lead. This results in a reasonably unified stylet and implanted lead structure whereby withdrawal of the stylet and of the implanted lead as a unit facilitates the complete removal of the implanted lead from the body. A threaded tip end of the stylet is used for threaded engagement with a tapped bore in the electrode. The threaded tip end of the stylet becomes locked to the electrode by rotating in one direction the threaded portion into the threaded bore and the stylet is removable by counter-rotating the threaded tip end of the stylet relative to the electrode.

This new lead extraction system mechanically locks the stylet into the lead distal tip to provide force and control at the location where the lead adheres to the myocardium. This invention will improve lead extraction in the form of fewer lead fractures, leaving no lead fragments in the heart as compared to existing lead extraction systems. If a decision is made to abort the lead removal, the threaded stylet can be unscrewed, leaving the lead unchanged. Also, inserting this extraction stylet would not require that the lead connector be cut off, which could also improve the situation if a lead extraction is aborted.

A primary feature, then, of the present invention is the provision of a technique for removal from a body of an implanted lead extending between distal and proximal ends.

Another feature of the present invention is the provision of such a technique, which facilitates the complete removal of the lead from the body.

Yet another feature of the present invention is the provision of such a technique according to which lead extraction is achieved by mechanically engaging the distal tip electrode and thereby eliminating the possibility of lead fracture and partial lead extraction.

Still a further feature of the present invention is the provision of such a technique according to which lead extraction can he aborted, leaving the lead unchanged.

Yet a further feature of the present invention is the provision of such a technique according to which cutting of the lead at the connector is not required as is currently required by known methods.

Still another feature of the present invention is the provision of such a technique according to which a known implant method and stylet will function properly with leads incorporating the novel concept of the invention.

Yet another feature of the present invention is the provision of such a technique according to which the electrode is actively fixed to body tissue.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENTS

Figure 1:
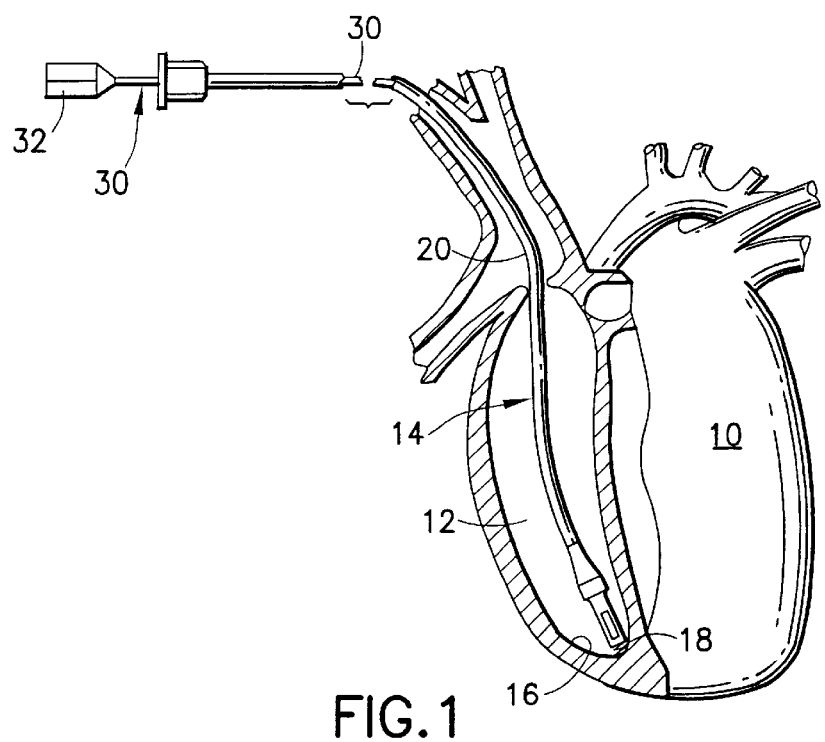
FIG. 1 is a perspective view illustrating a heart with a portion cut away to reveal an implantable lead assembly, embodying the present invention, secured therein to a wall of the heart.

Referring to FIG. 1, there is shown a diagrammatic perspective view partially cut away and shown in section of a heart 10 into the right ventricle 12 of which is inserted a body implantable lead 14 of the endocardial type incorporating features of the present invention. Although the present invention will be described with reference to the embodiments shown in the drawings, it should be understood that the present invention can be embodied in many alternate forms or embodiments. In addition, any suitable size, shape or type of elements or materials could be used. The lead 14 of an active fixation design is attached to an interior wall 16 of the heart 10 by means of a fixing helix 18, which engages the tissue or trabeculae of the heart.

Figure 2:
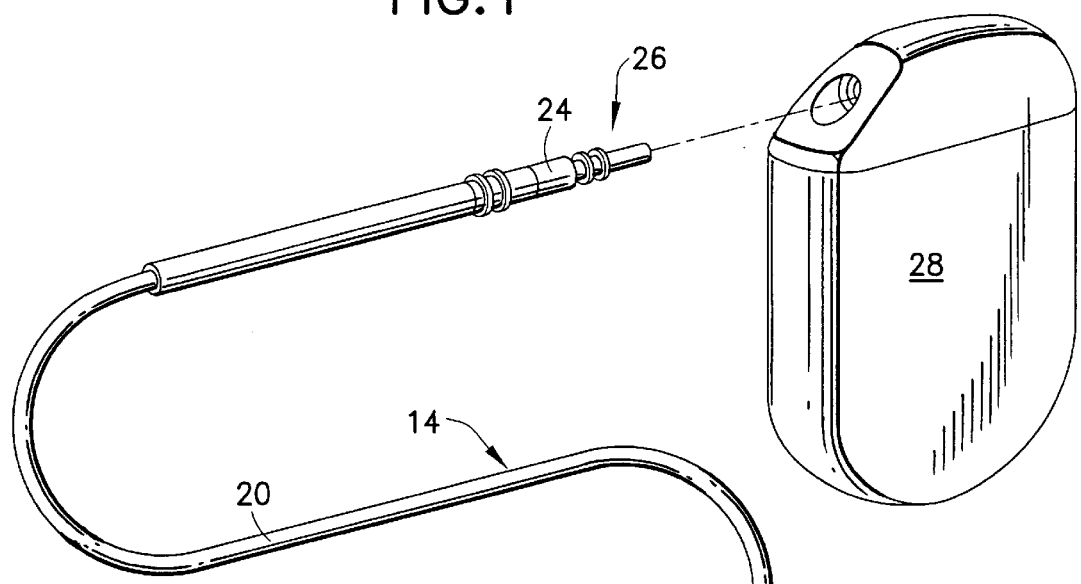
FIG. 2 is a perspective view of an implantable lead embodying the invention in combination with a stimulating device such as a pacemaker.
Figure 2:
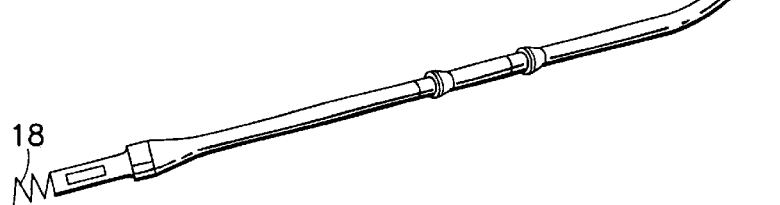

As further illustrated, the lead 14 also includes an insulating sheath 20 interconnecting the helix 18 secured to the interior wall 16 and an electrical connector 24 at a proximal end 26 to which can be attached a source of electrical energy such as a pacemaker 28 (FIG. 2). In FIG. 1, a stylet 30 is illustrated inserted within the insulating sheath 20 and may be used to provide rigidity to the lead 14 during insertion of the lead into the heart 10. However, in the present instance, concern is for removing the implanted lead 14 from a body or, more specifically, from an organ such as the heart 10.

Figure 3:
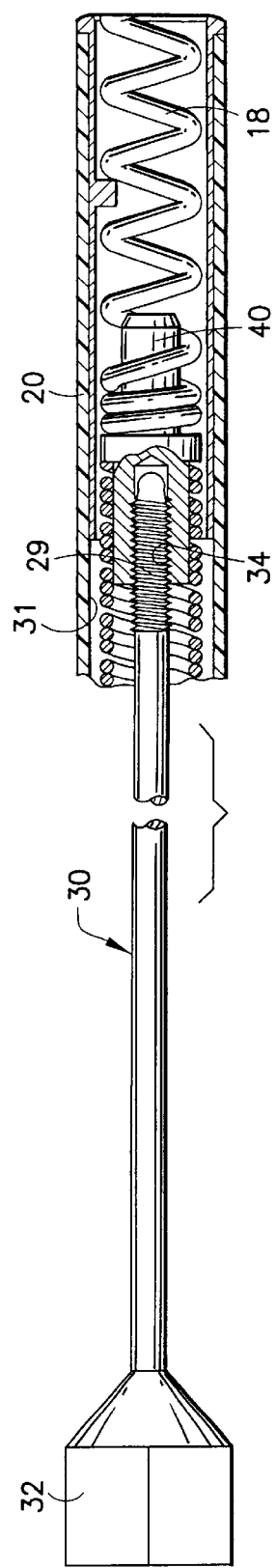
FIG. 3 is a side elevation view of a stylet constructed according to the present invention.

To this end, viewing FIG. 3, the elongated stylet 30 is illustrated as extending through a lumen 31 of the insulating sheath 20 between a distal attachment device, such as a threaded tip end 29, and a proximal manipulating device 32. The manipulating device is distant from the threaded tip end and may be a finger grip at a proximal extremity of the stylet 30 provided for controlling the introduction of the stylet into the lead 14 and its subsequent withdrawal. The threaded tip end 29 is provided for threaded engagement with a tapped bore 34 at the distal end of the implanted lead 14. When the stylet is so joined to the lead, the result is a reasonably unified stylet and implanted lead structure whereby withdrawal of the stylet and of the implanted lead as a unit facilitates the complete removal of the implanted lead from the body.

For this active fixation version of the lead designed to be used with a threaded stylet, the stylet is not utilized for the extension or retraction of the helix. Rather, in a known manner, the helix 18 is extended and retracted by turning a connector pin (not shown) which turns a conductor coil 38 about its longitudinal axis as well as the helix, resulting in extension and retraction of the helix in a known manner.

Figure 4:
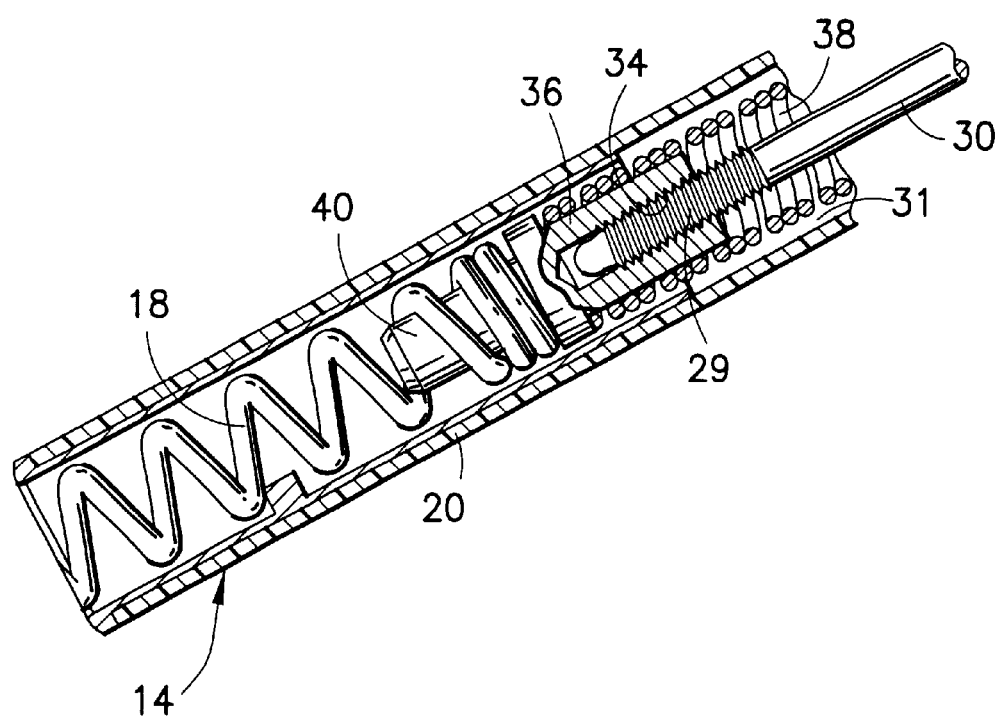
FIG. 4 is a detail cross section view of the distal end of an active fixation implantable lead embodying the invention.

Turn now to FIG. 4 for a more detailed explanation of a distal electrode design, which is suitable for the present invention.

In the instance illustrated in FIG. 4, the threaded tip end 29 of the stylet 30 is screwed into the tapped bore 34 of a weld electrode 36 and the weld electrode is integral with a distal shaft 40 to which the helix 18 is suitably fixed. The present invention applies force directly to the helix 18 compared to the current stylets used for lead extraction systems that lock onto a conductor coil 38. This extraction stylet 30 can also be removed by unscrewing it from the weld electrode 36 if a decision is made to abort the lead extraction. When the stylet is unscrewed, neither the weld electrode 36, nor the helix 18, nor the conductor coils 38, are damaged, and the stylet is removed as an entity.

It should be understood that the foregoing description is only illustrative of the invention. Various alternatives and modifications can be devised by those skilled in the art without departing from the invention. Accordingly, the present invention is intended to embrace all such alternatives, modifications and variances, which fall within the scope of the appended claims.

What is claimed is:

1. A removable implantable cardiac stimulation lead system for use with an implantable stimulation device, the lead system comprising:

a lead comprising a proximal connector coupled to an active fixation electrode by a conductor, the conductor being surrounded by an insulating sheath and comprising a lumen therein, the active fixation electrode comprising an extendable-retractable mechanism for activating the active fixation electrode by rotating the conductor, wherein the active fixation electrode further comprises a helix and a latching means accessible through the lumen, wherein the latching means comprises a distal shaft/electrode member having a distal portion coupled to the helix and a proximal portion coupled to the conductor; and a stylet comprising a stylet latching means at a distal end thereof, the stylet latching means being adapted to couple to the distal shaft/electrode member so that a predetermined pull force may be applied to remove the electrode from cardiac tissue without disengaging the stylet from the electrode;

wherein the stylet latching means is detachable;

wherein the stylet latching means comprises a threaded portion dimensioned to grip the electrode when the pull force is exerted; and wherein the distal shaft/electrode member comprises a corresponding threaded bore for receiving the threaded portion of the stylet which locks the distal end of the stylet to the distal shaft/electrode member by rotating the threaded portion into the threaded bore, wherein the stylet is removable by counter-rotating the threaded portion.

2. A removable implantable cardiac stimulation lead system for use with an implantable stimulation device, the lead system comprising:

a lead comprising a proximal connector coupled to an active fixation electrode by a conductor, the conductor being surrounded by an insulating sheath and comprising a lumen therein, the active fixation electrode comprising an extendable-retractable mechanism for activating the active fixation electrode by rotating the conductor, wherein the active fixation electrode further comprises a helix and a latching means accessible through the lumen, wherein the latching means comprises a distal shaft/electrode member having a distal portion coupled to the helix and a proximal portion coupled to the conductor; and a stylet comprising a stylet latching means at a distal end thereof, the stylet latching means being adapted to couple to the distal shaft/electrode member so that a predetermined pull force may be applied to remove the electrode from cardiac tissue without disengaging the stylet from the electrode;

wherein the stylet latching means is detachable;

wherein the stylet has a smooth outer peripheral surface adjacent its distal end;

wherein the distal shaft/electrode member has a longitudinal bore therein having a cylindrical wall;

wherein the stylet latching means comprises a first threaded portion dimensioned to grip the distal shaft/electrode member when the pull force is exerted; and wherein the distal shaft/electrode member comprises a second threaded portion which is threadedly engaged with the first threaded portion for locking the distal end of the stylet to the electrode by rotating the first threaded portion into the second threaded portion, wherein the stylet is removable by counter-rotating the first threaded portion.

3. A system comprising:

an implantable lead comprising a distal end that comprises an active fixation electrode adapted to be implanted in the body and further comprising a proximal end, wherein the lead comprises a distal shaft/electrode member at the distal end; and an elongated stylet comprising a proximal operating end and a distal attachment device that is releasably attachable to the distal shaft/electrode member of the implantable lead;

wherein the distal attachment device of the elongated stylet comprises a threaded tip end for threaded engagement with a tapped bore at the distal end of the implanted implantable lead;

wherein the threaded tip end is threadedly engaged with the tapped bore to lock the elongated stylet to the implantable lead by rotating the threaded tip end into the tapped bore; and wherein the elongated stylet is removable by counter-rotating the threaded tip end.

4. The system of claim 3, wherein the active fixation electrode comprises a helix.

5. A system comprising:

an implantable lead comprising a distal end that comprises an active fixation electrode adapted to be implanted in the body and further comprising a proximal end, wherein the implantable lead comprises a distal shaft/electrode member at the distal end; and an elongated stylet comprising a proximal operating end and a distal attachment device that is releasably attachable to the distal shaft/electrode member of the implantable lead;

wherein the stylet has a smooth outer peripheral surface adjacent its distal end;

wherein the distal shaft/electrode member comprises a weld electrode having a longitudinal bore therein with a cylindrical wall;

wherein the distal attachment device comprises a first threaded portion dimensioned to grip the weld electrode when the pull force is exerted; and wherein the distal shaft/electrode member comprises a second threaded portion which is threadedly engaged with the first threaded portion for locking the distal end of the stylet to the distal shaft/electrode member by rotating the first threaded portion into the second threaded portion, whereby the stylet is removable by counter-rotating the first threaded portion.

6. The system of claim 5, wherein the active fixation electrode comprises a helix.

7. An implantable cardiac lead system, comprising:

a lead comprising:
  a helix;
  a distal shaft/electrode member, a distal portion of the distal shaft/electrode member coupled to a proximal portion of the helix;
  a conductor, a distal portion of the conductor coupled to a proximal portion of the distal shaft/electrode member; and
  an electrical connector, a proximal portion of the conductor coupled to the electrical connector; and a stylet having a coupler, the coupler disposed at a distal portion of the stylet, the coupler lockingly engaging with the distal shaft/electrode member so that a predetermined pull force may be applied to remove the lead from cardiac tissue without disengaging the stylet from distal shaft/electrode member;

wherein the distal/shaft electrode member has a threaded bore; and wherein the coupler has a threaded tip to lock with the threaded bore of the distal/shaft electrode member.

8. The lead system of claim 7, wherein the conductor is a coil conductor.

* * * * *